(12) United States Patent
Akiyama et al.

(10) Patent No.: US 8,253,930 B2
(45) Date of Patent: Aug. 28, 2012

(54) ABSORPTION SPECTROMETRIC APPARATUS FOR SEMICONDUCTOR PRODUCTION PROCESS

(75) Inventors: Osamu Akiyama, Kyoto (JP); Masashi Akimoto, Kyoto (JP); Tsuyoshi Moriya, Tokyo (JP); Jun Yamawaku, Nirasaki (JP)

(73) Assignees: Shimadzu Corporation, Kyoto (JP); Tokyo Electron Limited, Tokyo (JP)

( * ) Notice: Subject to any disclaimer, the term of this patent is extended or adjusted under 35 U.S.C. 154(b) by 374 days.

(21) Appl. No.: 12/707,418

(22) Filed: Feb. 17, 2010

(65) Prior Publication Data

US 2010/0214557 A1    Aug. 26, 2010

(30) Foreign Application Priority Data

Feb. 20, 2009    (JP) ................. 2009-037549

(51) Int. Cl.
*G01N 21/00*    (2006.01)
(52) U.S. Cl. ........................................ 356/73
(58) Field of Classification Search .............. 356/72–73, 356/437, 440, 246, 244; 438/16
See application file for complete search history.

(56) References Cited

U.S. PATENT DOCUMENTS

| | | | |
|---|---|---|---|
| 5,746,829 A | 5/1998 | Matsunaga et al. | |
| 5,963,336 A | 10/1999 | McAndrew et al. | |
| 6,442,736 B1 | 8/2002 | Girard et al. | |
| 7,033,843 B2 * | 4/2006 | Hasegawa et al. | ............ 438/11 |

FOREIGN PATENT DOCUMENTS

| | | |
|---|---|---|
| CN | 1155655 A | 7/1997 |
| JP | 5-99845 A | 4/1993 |
| JP | 11-183366 A | 7/1999 |
| JP | 2001-244202 A | 9/2001 |
| KR | 10-2002-0026857 A | 4/2002 |

OTHER PUBLICATIONS

The First Office Action for the Application No. 201010121550.0 from State Intellectual Property Office of People's Republic of China dated Mar. 22, 2011.
Herriott, D. et al., "Off-Axis Paths in Spherical Mirror Interferometers", Applied Optics, 1964, vol. 3, No. 4, pp. 523-526.
Korean Office Action for Application No. 10-2010-0008254 dated Nov. 16, 2011.

* cited by examiner

*Primary Examiner* — Tarifur Chowdhury
*Assistant Examiner* — Abdullahi Nur
(74) *Attorney, Agent, or Firm* — Cheng Law Group, PLLC

(57) ABSTRACT

This absorption spectrometric apparatus for semiconductor production process includes a flow passageway switching mechanism connected to a discharging flow passageway of a processing chamber for a semiconductor production process and a multiple reflection type moisture concentration measuring absorption spectrometric analyzer that allows a laser beam from a laser light source to undergo multiple reflection within a cell, detects a light absorbancy change by a gas within the cell, and measures a moisture concentration within the gas. The flow passageway switching mechanism connects the discharging flow passageway by switching between a measuring flow passageway through which the gas is discharged by passing through the cell and a bypass flow passageway through which the gas is discharged without passing through the cell.

5 Claims, 2 Drawing Sheets

ABSORPTION SPECTROMETRIC APPARATUS FOR SEMICONDUCTOR PRODUCTION PROCESS

BACKGROUND OF THE INVENTION

1. Field of the Invention

The present invention relates to an apparatus for measuring a moisture content within a gas by using a laser beam. For example, the present invention relates to an absorption spectrometric apparatus for semiconductor production process that is used for monitoring the moisture content within a process gas at all times for suppressing the moisture concentration within the process gas to be less than or equal to a predetermined value in a semiconductor production line.

2. Description of the Related Art

In a semiconductor production process, various fine processings and treatments are carried out on a semiconductor substrate (silicon wafer) surface. During that time, various process gases are used, such as an etching gas, a reaction gas for epitaxial growth, and a reaction gas for CVD (chemical vapor deposition). It is known in the art that, when moisture is contained in these process gases, the process gases and moisture, or the substrate surface and moisture react with each other to produce an unnecessary byproduct, whereby the yield of the produced semiconductor decreases considerably.

For this reason, in order to ensure stability of the processing in a semiconductor production process, one considers attaching a process monitor to the semiconductor production apparatus. As one of these, a measure of attaching a monitor to a discharging outlet of the process gas of the semiconductor production apparatus and grasping the state of the semiconductor production process by monitoring the components of the discharged gas, thereby to improve the yield both within a lot and between the lots and to achieve stabilization of the process is proposed.

Typically, as the process gas, a highly reactive gas is often used. For this reason, various substances such as reactive byproducts including a highly corrosive gas, unreacted substances, and moisture are mingled within the discharged gas. In the case of monitoring the discharged gas, measures both in hardware and in software are needed in the measuring system thereof.

As a monitor of the discharged gas, particularly a moisture monitor is important. As a method of measuring the moisture concentration contained in the process gas, a quartz oscillation type method that measures the frequency change of a quartz oscillator, and an electrostatic capacitance type method that measures the electrostatic capacitance change by allowing the moisture within the gas to be adsorbed are known. Also, a laser aquameter that measures the moisture concentration by infrared spectrophotometry using a laser of variable wavelength type (See Japanese Patent Application Laid-open Nos. 05-99845 and 11-183366) is proposed.

The above-described laser aquameter is such that the moisture concentration is determined by the intensity of a laser beam at the moisture absorption wavelength by introducing a sample gas into a sample cell, allowing a laser beam having a predetermined wavelength to be incident into the sample cell, and analyzing a transmitted laser beam. Since the measurement can be made without letting the sensor part be in contact with the measurement object gas, the laser aquameter can be applied to a corrosive gas unlike those of the quartz oscillation type or the electrostatic capacitance type, and is also characterized in that the response speed is high.

Also, as a discharged gas analyzing cell in the above-described laser aquameter, in order to raise the analyzing sensitivity, those of a White type, a Herriott type in which reflection is made for plural times between two opposing mirrors, or the like are used (See D. R. Herriott, H. Kogelnik, and R. Kompfer, Appl. Opt. 3, 523 (1964)).

BRIEF SUMMARY OF THE INVENTION

Various substances are contained within a discharged gas in a semiconductor production process, and these adhere to a reflection mirror or a window within the cell of an aquameter to cause decrease in the reflectivity or transmissivity in the optical system, thereby disadvantageously leading to decrease in the analyzing sensitivity.

An object of the present invention is to suppress the sensitivity decrease of an aquameter used as a discharged gas monitor for a semiconductor production process.

Among the various substances in a discharged gas, those having the largest influence on the decrease of the analyzing sensitivity of an aquameter are particles (powdery particulate substances). It is a comparatively rare case that particles are generated continuously. Particles are often generated at specific timing points such as immediately after a gate valve between a load lock chamber and a processing chamber is opened, or immediately after a reactive gas is introduced. Therefore, the present invention has been made so that the particles that affect the moisture concentration measurement may not be mingled.

An absorption spectrometric apparatus for semiconductor production process of the present invention includes a flow passageway switching mechanism connected to a discharging flow passageway of a processing chamber for a semiconductor production process and an absorption spectrometric analyzer connected to the discharging flow passageway via the flow passageway switching mechanism.

The absorption spectrometric analyzer is a multiple reflection type moisture concentration measuring absorption spectrometric analyzer including a cell that passes a process gas discharged from the discharging flow passageway therethrough and an optical system that allows a laser beam from a laser light source to undergo multiple reflection within the cell and detects a light absorbancy change by the process gas within the cell, so as to measure a moisture concentration within the process gas.

The flow passageway switching mechanism connects the discharging flow passageway by switching between a measuring flow passageway through which the gas is discharged by passing through the cell of the absorption spectrometric analyzer and a bypass flow passageway through which the gas is discharged without passing through the cell.

When the generation of particles is above or equal to a predetermined level, the discharged gas having a high particle concentration is let through the bypass flow passageway, so as to prevent the particles from adhering to the optical element surface within the analyzer, whereby the moisture concentration can be measured at a high precision by suppressing the sensitivity decrease.

The processing chamber preferably includes a particle counter that measures the number of particles contained in the process gas. In this case, the flow passageway switching mechanism can use a result of measuring the number of particles by the particle counter as a determination standard for flow passageway switching.

In order to prevent the mingling of the particles into the analyzer automatically, the absorption spectrometric apparatus may further include a controlling unit connected to be capable of communication with the flow passageway switching mechanism, the particle counter, and the analyzer, and the controlling unit may automatically switch the flow passageway switching mechanism so that the discharging flow passageway may be connected to the bypass flow passageway through which the gas is discharged without passing through the analyzer when the particle counter detects particles in a concentration equal to or higher than a predetermined value in the process gas, thereby preventing the particles from adhering to the inside of the analyzer. This allows the mingling of particles into the analyzer to be automatically prevented, and the operation can be simplified.

DETAILED DESCRIPTION OF THE INVENTION

Hereinafter, an example of the present invention will be described.

Figure 1:
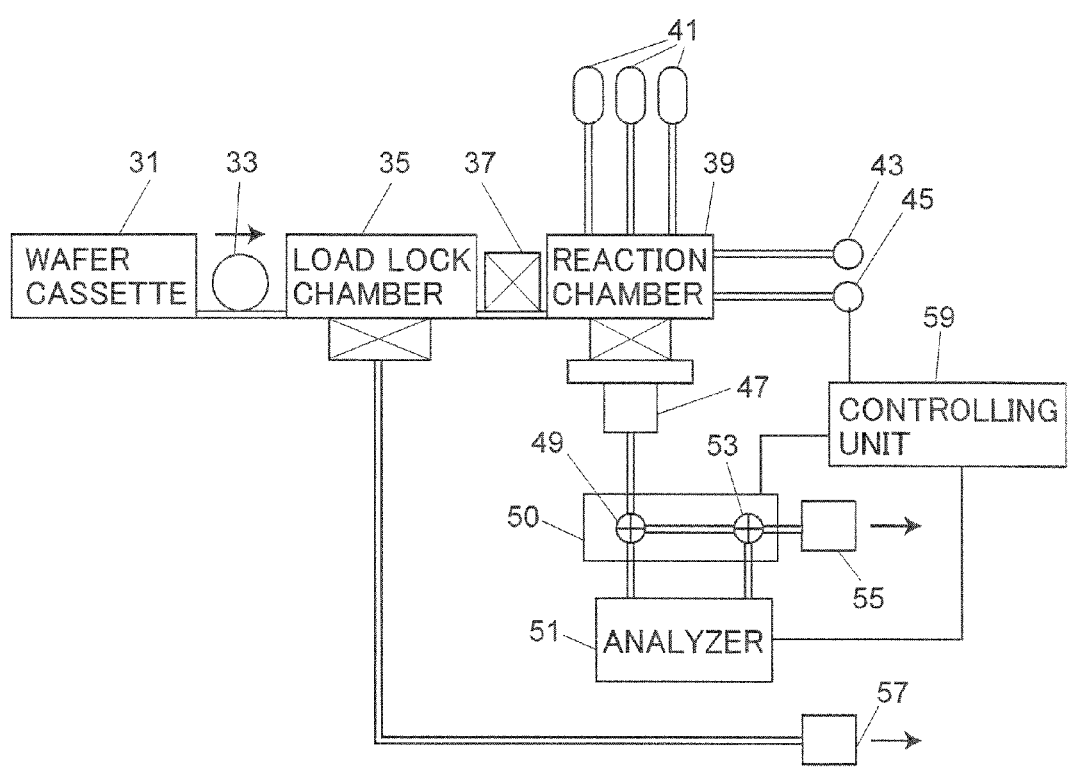
FIG. 1 is a schematic view illustrating one example of the present invention.

FIG. 1 is a schematic view of an absorption spectrometric apparatus for monitoring a semiconductor production process. A silicon wafer 33 accommodated in a wafer cassette 31 is put into a load lock chamber 35 so as to be moved to a reduced-pressure environment. A dry pump 57 is connected to the load lock chamber 35, whereby the inside of the load lock chamber 35 can be reduced in pressure.

The load lock chamber 35 is connected via a gate valve 37 to a reaction chamber (processing chamber) 39 for processing a process gas to the silicon wafer. The gate valve 37 is opened when the pressure of the load lock chamber 35 is a pressure (typically 100 mTorr to 50 mTorr) under which the wafer can be transferred into the reaction chamber 39.

A main discharging pump 47 capable of discharging the gas within the reaction chamber 39 to a high vacuum degree and a low-vacuum rough-drawing dry pump 55 disposed on the downstream side of the main discharging pump 47 are connected to a discharging outlet of the reaction chamber 39. The main discharging pump 47 and the dry pump 55 are both used for reducing the pressure inside the reaction chamber 39.

Various reactive, gases used for plasma processing are supplied via valves 41 to the reaction chamber 39, whereby the wafer can be processed using the various process gases. Also, a vacuum gauge 43 and a particle counter 45 are connected to the reaction chamber 39. The vacuum gauge 43 is adapted to be capable of measuring the vacuum degree within the reaction chamber 39, and the particle counter 45 is adapted to be capable of measuring the number of particles within the reaction chamber 39.

A flow passageway switching mechanism 50 is connected between the main discharging pump 47 and the dry pump 55. The flow passageway switching mechanism 50 includes a switching valve 49 connected to the main discharging pump 47 and a switching valve 53 connected to the dry pump 55 side. The switching valve 49 is connected to a sample gas introduction inlet of a cell of an analyzer 51, and the switching valve 53 is connected to the discharging outlet of the cell. A short-circuit flow passageway is connected between the two switching valves 49, 53. The two switching valves 49, 53 are switched between a mode constituting a measuring flow passageway through which the gas discharged from the reaction chamber 39 is discharged by passing through the cell of the analyzer 51 and a mode constituting a bypass flow passageway that forms a short circuit between the two switching valves 49, 53 without passing through the cell of the analyzer 51. As the switching valves 49, 53, it is possible to use a three-way valve (for example, SS68-XTF32 manufactured by Swagelock Co., Ltd.) or the like.

A controlling unit 59 is connected to the particle counter 45, the flow passageway switching mechanism 50, and the analyzer 51 to be capable of communication therewith.

Figure 2:
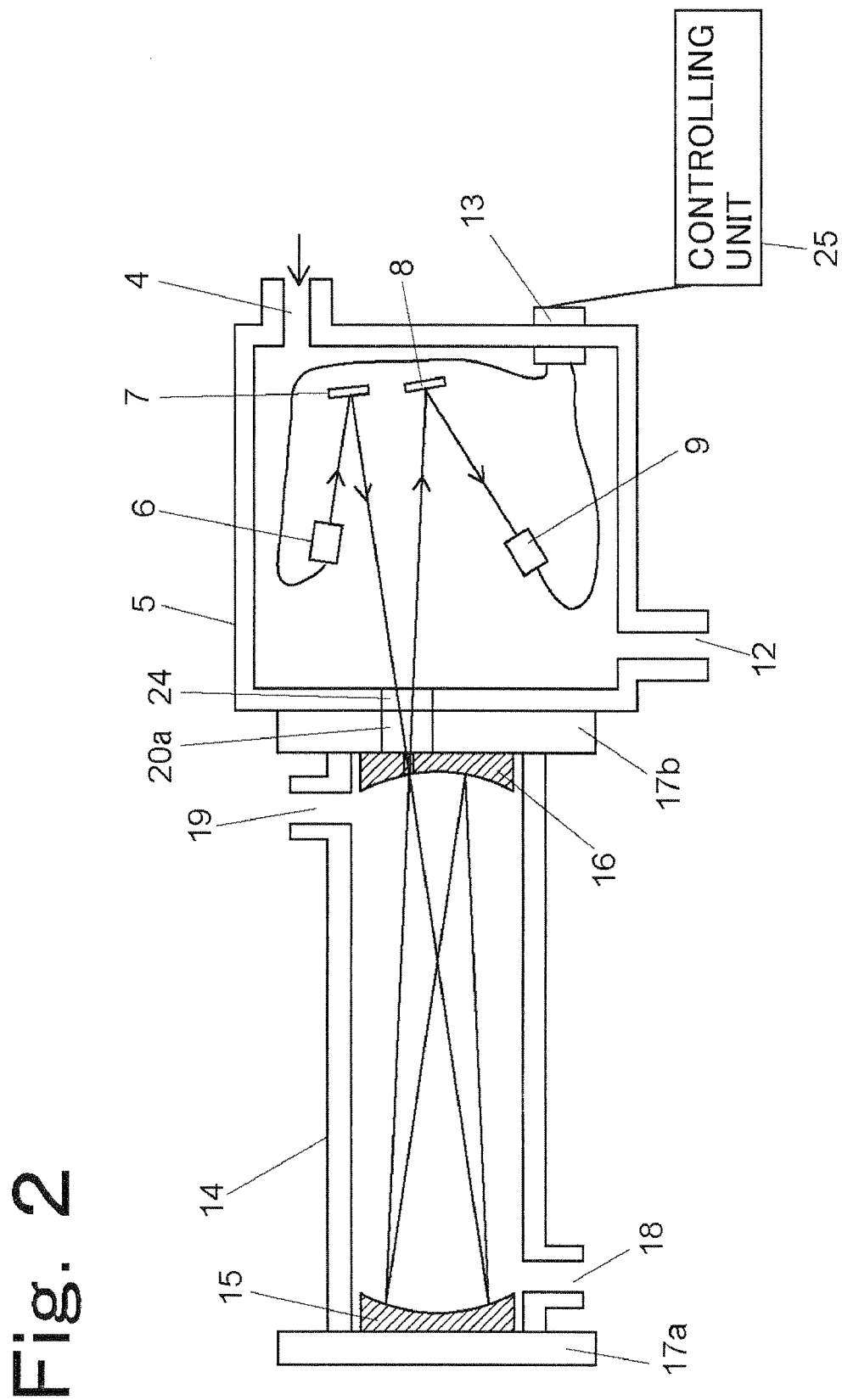
FIG. 2 is a schematic cross-sectional view illustrating one example of a multiple reflection type moisture concentration measuring absorption spectrometric analyzer.

As the analyzer 51, a multiple reflection type moisture concentration measuring absorption spectrometric analyzer is used. Next, the multiple reflection type moisture concentration measuring absorption spectrometric analyzer used as the analyzer 51 will be described. FIG. 2 is a schematic cross-sectional view of the absorption spectrometric analyzer.

At both ends in the inside of a multiple reflection cell 14 into which the sample gas is introduced, a pair of opposing concave mirrors 15, 16 are disposed for multiple reflection of an incident laser beam. The mirrors 15, 16 are mounted respectively to flanges 17a, 17b.

A light source chamber 5 for radiating the laser beam is disposed to be adjacent to the flange 17b on the mirror 16 side of the cell 14. A light transmitting window 20a is provided in the mirror 16 and the flange 17b for entering and exiting of the laser beam, and also a light transmitting window 24 is provided in the wall surface of the light source chamber 5 corresponding to the light transmitting window 20a for entering and exiting of the laser beam. Into one of or both of the light transmitting windows 20a and 24, a window plate made of a quartz plate or the like having a light transmitting property to the laser beam is fitted, so as to seal between the cell 14 and the light source chamber 5 in an air-tight manner. In the inside of the light source chamber 5, a light source unit 6, a mirror 7 for reflecting the laser beam radiated from the light source unit 6 so as to introduce the laser beam through the light transmitting windows 24, 20a into the cell 14, a detecting unit 9 made of a photodiode or the like, and a mirror 8 for introducing the laser beam subjected to multiple reflection by the mirrors 15, 16 in the cell 14 and exiting through the light transmitting windows 20a, 24 to the detecting unit 9 are provided.

As a light source of the light source unit 6, a laser light source is used. This is due to the following reason. With a lamp light source such as a halogen lamp, divergence of the luminous flux will be large after multiple reflections between the mirrors 15, 16, so that it is not possible to take out a sufficient light quantity.

The light source unit 6 and the detecting unit 9 are connected, via a connector 13 disposed on the side surface of the light source chamber 5, to a controlling unit 25 that scans the wavelength of the laser beam at a predetermined scanning frequency. The controlling unit 25 is connected to the controlling unit 59 in FIG. 1

The cell 14 is provided with a sample gas introducing inlet 18 for introducing a sample gas and a sample gas discharging outlet 19 for discharging the sample gas. The sample gas introducing inlet 18 and the sample gas discharging outlet 19 are connected respectively to the switching valve 49 and the switching valve 53 in FIG. 1.

In order to keep the inside of the light source chamber 5 in a dry state, the light source chamber 5 is provided with a purge gas introducing inlet 4 for introducing a purge gas and a purge gas discharging outlet 12 for discharging the purge gas, whereby a dry gas such as $N_2$ is introduced from the purge gas introducing inlet 4 and discharged from the purge gas discharging outlet 12.

Next, an operation of the example will be described.

[Semiconductor Production Process]

The wafer 33 is transferred from the wafer cassette 31 to the load lock chamber 35. The pressure in the load lock chamber 35 accommodating the wafer 33 is reduced to a pressure (typically 100 mTorr to 50 mTorr) at which the wafer 33 can be transferred to the reaction chamber 39. After the pressure is reduced in the load lock chamber 35, the gate valve 37 that partitions between the load lock chamber 35 and the reaction chamber 39 is opened, so as to transfer the wafer into the reaction chamber 39.

Since the pressure inside the reaction chamber 39 is subjected to a little fluctuation in introducing the wafer, the pressure has been reduced to a predetermined pressure (typically several mTorr to several hundred µTorr) by the main discharging pump 47. Thereafter, the reactive gases are introduced via the valves 41 into the reaction chamber 39, and a plasma is ignited to perform plasma processing on the wafer.

In the reaction chamber 39, processing is carried out in a complex reaction system such as between a wafer surface and a reaction gas excited by the plasma and between the plurality of excited reaction gases. During the processing, the gas in the reaction chamber 39 is discharged at all times by the main discharging pump 47, and unnecessary substances (for example, unreacted gases, reaction products, radicals, and others) are discharged and removed while the gas passes through the analyzer 51 for monitoring of the moisture.

[Moisture Concentration Measurement]

In FIG. 2, the dry gas is introduced from the purge gas introducing inlet 4 of the light source chamber 5 and discharged from the purge gas discharging outlet 12. Preferably, the inside of the light source chamber 5 is sufficiently purged and reduced in pressure so that components such as moisture may not adhere thereto.

The process gas serving as the sample gas is let to flow from the sample introducing inlet 18 of the cell 14 and the moisture in the process gas is measured. The laser beam exiting from the light source unit 6 within the light source chamber 5 is reflected by the mirror 7 to go toward the multiple reflection cell 14. After passing through the light transmitting windows 24, 20a, the laser beam will first be incident onto the mirror 15 among the mirrors 15, 16 that are disposed to oppose each other. Thereafter, the laser beam undergoes multiple reflections between the mirror 15 and the mirror 16. The laser beam subjected to multiple reflection is taken out from the light transmitting windows 20a, 24, is incident onto the mirror 8 within the light source chamber 5 to be reflected, and is incident into the detecting unit 9 to undergo photoelectric conversion, whereby the moisture concentration is measured. The moisture concentration can be determined by the damping of the light quantity of the laser beam within the cell 14.

[Flow Passageway Switching]

The number of particles in the gas within the reaction chamber 39 is counted by the particle counter 45 connected to the reaction chamber 39. When the number of particles is measured to exceed a predetermined level, the flow passageway switching mechanism 50 is switched, so as to let the discharged gas from the reaction chamber 39 flow through the bypass flow passageway that does not pass through the analyzer 51. The particle number or the particle concentration serving as the determination standard for switching the flow passageway switching mechanism 50 is preferably defined beforehand by an experiment.

Various substances are contained in a discharged gas in a semiconductor production process. By measuring the moisture concentration, it is possible to determine whether the process is being carried out appropriately or not.

In the present example, the switching valves 49, 53 are disposed between the main discharging pump 47 and the analyzer 51, whereby the discharged gas from the reaction chamber 39 can flow by selection between the measuring flow passageway that passes through the analyzer 51 and the bypass flow passageway that does not pass through the analyzer 51. This allows the sample gas to be introduced into the analyzer 51 at a timing and a quantity (time control) that meets individual semiconductor production processes and the characteristics of monitoring.

For the switching of the switching valves 49, 53, the timing of the switching may be determined in real time by feeding a result of measurement obtained from the particle counter 45 mounted on the reaction chamber 39 back to the controlling unit 59. Alternatively, a dummy test may be carried out to determine a switching timing of the switching valves 49, 53 in advance from a result of measurement obtained from the particle counter, and the switching valves 49, 53 may be switched either manually or automatically at the timing determined in advance.

What is claimed is:

1. An absorption spectrometric apparatus for semiconductor production process, comprising:
    a flow passageway switching mechanism connected to a discharging flow passageway of a processing chamber for a semiconductor production process; and
    a multiple reflection type moisture concentration measuring absorption spectrometric analyzer connected to the discharging flow passageway via the flow passageway switching mechanism, and including a cell that passes a process gas discharged from the discharging flow passageway therethrough and an optical system that allows a laser beam from a laser light source to undergo multiple reflection within the cell and detects alight absorbancy change by the process gas within the cell, so as to measure a moisture concentration within the process gas,
    wherein the flow passageway switching mechanism connects the discharging flow passageway by switching between a measuring flow passageway through which the gas is discharged by passing through the cell of the absorption spectrometric analyzer and a bypass flow passageway through which the gas is discharged without passing through the cell.

2. The absorption spectrometric apparatus according to claim 1, wherein the processing chamber includes a particle counter that measures the number of particles contained in the process gas.

3. The absorption spectrometric apparatus according to claim 2, further comprising a controlling unit connected to be capable of communication with the flow passageway switching mechanism, the particle counter, and the absorption spectrometric analyzer,
    wherein the flow passageway switching mechanism connects the discharging flow passageway to the measuring flow passageway while the moisture concentration within the process gas is being measured, and
    the controlling unit switches the flow passageway switching mechanism from the measuring flow passageway to the bypass flow passageway when the particle counter detects particles in an amount equal to or larger than a predetermined value in the process gas.

4. The absorption spectrometric apparatus according to claim 1, wherein a main discharging pump disposed on the processing chamber side and a rough-drawing dry pump disposed on the downstream side of the main discharging pump are connected to the discharging flow passageway, and the flow passageway switching mechanism is disposed between the main discharging pump and the rough-drawing dry pump.

5. The absorption spectrometric apparatus according to claim 4, wherein the flow passageway switching mechanism includes a first switching valve disposed on the main discharging pump side and a second switching valve connected to the dry pump side, where the first switching valve is connected to a gas introducing inlet of the cell; the second switching valve is connected to a gas discharging outlet of the cell; and a short-circuit flow passageway is connected between the two switching valves, whereby, by switching between the two switching valves, the measuring flow passageway is constructed as a flow passageway for the gas discharged from the processing chamber to pass through the cell, and the bypass flow passageway is constructed as a flow passageway for the gas discharged from the processing chamber to pass through the short-circuit flow passageway between the two switching valves without passing through the cell.

* * * * *